US008227574B2

(12) United States Patent
Paukshto et al.

(10) Patent No.: US 8,227,574 B2
(45) Date of Patent: Jul. 24, 2012

(54) COLLAGEN MATERIALS, FILMS AND METHODS OF MAKING SAME

(75) Inventors: Mikhail Vitoldovich Paukshto, Foster City, CA (US); David Harwood McMurtry, Felton, CA (US); Gerald G. Fuller, Stanford, CA (US); Yuri Alexandrovich Bobrov, Menlo Park, CA (US); John E. Kirkwood, Santa Clara, CA (US)

(73) Assignees: Fibralign Corporation, Sunnyvale, CA (US); The Board of Trustees of the Leland Stanford Junior University, Stanford, CA (US)

( * ) Notice: Subject to any disclaimer, the term of this patent is extended or adjusted under 35 U.S.C. 154(b) by 1243 days.

(21) Appl. No.: 11/951,324

(22) Filed: Dec. 5, 2007

(65) Prior Publication Data

US 2011/0151563 A1    Jun. 23, 2011

Related U.S. Application Data

(60) Provisional application No. 60/872,773, filed on Dec. 5, 2006, provisional application No. 60/880,703, filed on Jan. 17, 2007.

(51) Int. Cl.
*A61K 38/17* (2006.01)
(52) U.S. Cl. ....................................................... 530/356
(58) Field of Classification Search ........................ None
See application file for complete search history.

(56) References Cited

U.S. PATENT DOCUMENTS

| 4,869,200 | A | 9/1989 | Euverard |
|---|---|---|---|
| 6,737,053 | B1 | 5/2004 | Goh et al. |
| 6,824,716 | B2 | 11/2004 | Liao et al. |
| 7,338,517 | B2 | 3/2008 | Yost et al. |
| 7,354,627 | B2 | 4/2008 | Pedrozo et al. |
| 2005/0019488 | A1 | 1/2005 | Braithwaite et al. |
| 2008/0115724 | A1 | 5/2008 | McMurtry et al. |

FOREIGN PATENT DOCUMENTS

| EP | 0 518 697 A2 | 12/1992 |
|---|---|---|
| JP | 2004-148014 A | 5/2004 |

OTHER PUBLICATIONS

International Search Report and Written Opinion received in PCT patent application No. PCT/US2007/025037, dated Apr. 8, 2008.
Wei Tan and Tejal A. Desai; "Layer-by-layer Microfluidics for Biomimetic Three-Dimensional Structures"; (2004); vol. 25; pp. 1355-1364; Biomaterials.
Besseau, L. et al., "Production of Ordered Collagen Matrices for Three-Dimensional Cell Culture," Biomaterial, 23, 2002, pp. 27-36.
Cisneros, D. et al., "Creating Ultrathin Nanoscopic Collagen Matrices for Biological and Biotechnological Applications", Wiley InterScience, 2007, vol. 3, No. 6, pp. 956-963.
Cowin, S., "Do Liquid Crystal-Like Flow Processors Occur in the Supramolecular Assembly of Biological Tissues?", J. Non-Newtonian Fluid Mech. 119, 2004, pp. 155-162.
Eglin, D. et al., "Type I Collagen, a Versatile Liquid Crystal Biological Template for Silica Structuration from Nano-to Microscopic Scales," The Royal Society of Chemistry 2005, 1, pp. 129-131.
Evans, H., et al. "Novel 3D Culture System for Study of Cardiac Myocyte Development," Am J. Physiol Heart Circ Physiol 285: 2003, H570-H578.
Fennell, L., et al., "Thin Crystal Film Polarizers," Asia Display/IDW '01, pp. 601-603, 2001.
Gobeaux, F., Cooperative Ordering of Collagen Triple Helices in the Dense State, Langmuir 2007, vol. 23, pp. 6411-6417.
Guo, C. et al., "Flow and Magnetic Field Induced Collagen Alignment", Biomaterials 28, 2007, pp. 1105-1114.
Knight, D. et al. "Biological Liquid Crystal Elastomers", Philosophical Transactions: Biological Sciences, vol. 357, No. 1418, Estomeric Proteins: Structures, Biomechanical Properties and Biological Roles. Feb. 28, 2002, pp. 155-163.
Martin, R. et al., "Liquid Crystalline Ordering of Procollagen as a Determinant of Three-Dimensional Extracellular Matrix Architecture", J. Mol. Biol. 2000, 301, pp. 11-17.
Ng, C. P., et al., "Fibroblast Alignment Under Interstitial Fluid Flow Using a Novel 3-D Tissue Culture Model", Am J. Physical Heart Circ. Physiol 284: Jan. 16, 2003, pp. H1771-H1777.
Paukshto, M., et al., "Optics of Sheared Liquid-Crystal Polarizer Based on Aqueous Dispersion of Dichroic-Dye Nano-Aggregates", Journal of the SID, 13/9, 2005, pp. 765-772.
Yoshizato, K. et al., "In Vitro Orientation of Fibroblasts and Myoblasts on Aligned Collagen Film", Develop., Growth and Differ., 23 (2), 1981, pp. 175-184, 1981.
Zhong, S. et al., "An Aligned Nanofibrous Collagen Scaffold by Electrospinning and its Effects on In Vitro Fibroblast Culture", Journal of Biomedical Materials Research Part A, 2006 Wiley Periodicals, Inc., pp. 456-463.

*Primary Examiner* — Suzanne M Noakes
(74) *Attorney, Agent, or Firm* — Nixon Peabody LLP

(57) ABSTRACT

In general, the present invention is related to collagen compositions and thin films, and to methods of making and using the same. In some embodiments, the present invention is directed to "woven pattern" or "basket pattern" collagen compositions and thin films, and methods of making.

25 Claims, 7 Drawing Sheets

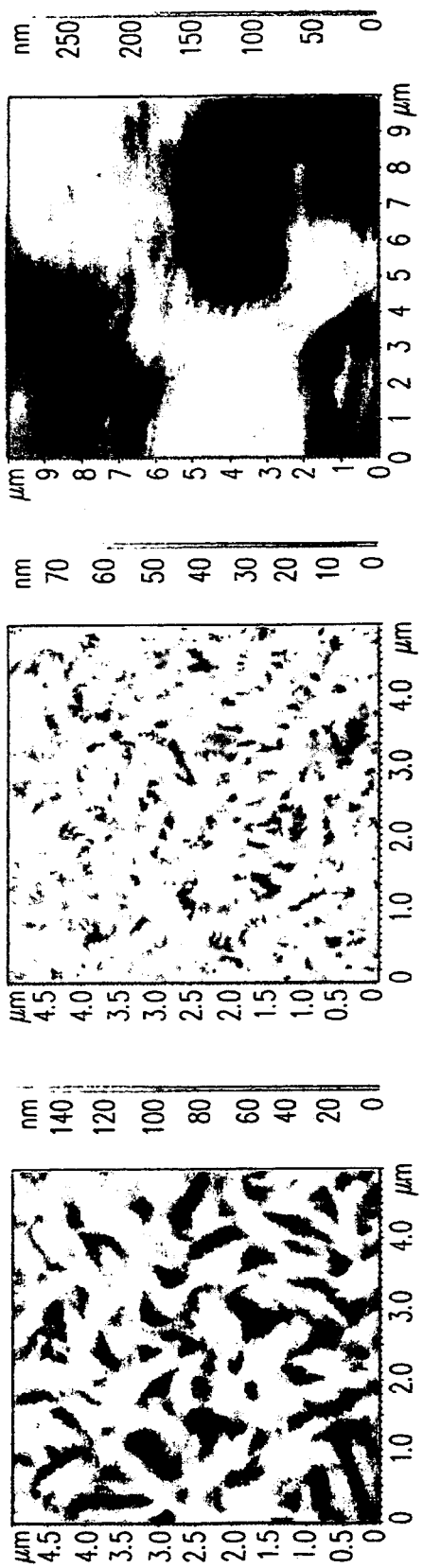
FIG. 6C
FIG. 6B
FIG. 6A
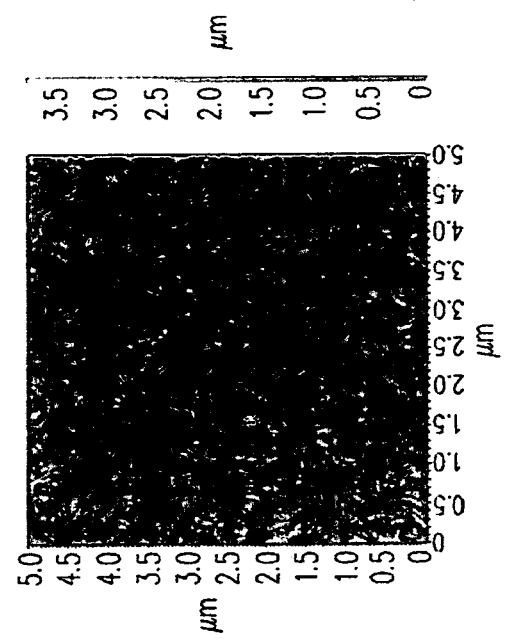
FIG. 7

| | 2x2 micron | 5x5 micron | 10x10 micron |
|---|---|---|---|
| Amount of sampling | 65536 | 262144 | 65536 |
| Max | 158.16 nm | 170.32 nm | 144 nm |
| Min | 0 nm | 0 nm | 0 nm |
| Peak-to-peak, Sy | 158.16 nm | 170.32nm | 144 nm |
| Ten point height, Sz | 79.72 nm | 85.376 nm | 73.272 nm |
| Average | 111.358 nm | 123.868 nm | 102.149 nm |
| Average Roughness, Sa | 17.7709 nm | 17.1241 nm | 15.0967 nm |
| Second moment | 113.902 | 125.876 | 104.035 |
| Root Mean Square, Sq | 23.9365 nm | 22.3905 nm | 19.7232 nm |

COLLAGEN MATERIALS, FILMS AND METHODS OF MAKING SAME

CROSS REFERENCE TO RELATED APPLICATIONS

This application claims the benefit of, and priority to, U.S. Provisional Patent Application Ser. Nos. 60/872,773 filed on Dec. 5, 2006 and 60/880,703 filed on Jan. 17, 2007, the entire disclosures of both of which are hereby incorporated by reference in their entireties.

FIELD OF THE INVENTION

In general, the present invention is related to collagen materials, compositions and films, and to methods of making and using the same. In some embodiments, the present invention is directed to "woven pattern" or "basket pattern" or "basket weave" collagen materials, compositions and thin films, and methods of making.

BACKGROUND OF THE INVENTION

There are more than twenty genetically distinct collagens in the body characterized by different genes, different amino acid sequences, different structures and different histological locations but with common features including being triple helical molecules with high glycine and praline content in the triple helical domains. Collagen type 1 (hereinafter "Collagen 1") is the most abundant of the collagens and is found in large quantities in tendon, bone, skin, cornea and other sites. Collagen 1 fibers can be identified by a 67 nm periodicity, by immunoreactivity to specific antibodies and by staining with various dyes. The collagen fibril serves as one of the prominent scaffolding structures utilized in animals, where the strength of an individual ropelike collagen molecule relates directly to the structural integrity and strength of the tissue. Collagen 1 fibrils are substantial constituents of skin, tendon, bone, ligament, cornea, where the fundamental tensile properties of the fibril are finely tuned to serve bespoke biomechanical, structural, and mechanotransductory signaling roles. Many of these properties derive from the structural organization within a fibril, where the organization and topology of the collagen molecules ensure strong intermolecular interactions which are further stabilized by covalent crosslinks derived from lysines in the molecule. The presence of subfibrillar organization may point to structural levels of organization that are required for the successful mechanical response of fibrillar collagens, and may also be part of the inevitable balance between crystallinity and disorder within a biological polymer.

The principles for the self-assembly of collagen fibrils into structures resembling those found in vivo remain a mystery, though the importance of liquid crystal-like arrangements of the collagen as secreted by organized groups of cells represents a current model.

The assembly of Collagen 1 into fibril has long been regarded as a spontaneous self-assembly process, the limitation of fibril size could be ascribed to a physical equilibrium between soluble procollagen molecules and the growing insoluble fibril. Fibril-forming collagens are synthesized as precursor procollagens, where N- and C-terminal globular propeptide extensions maintain solubility. The C-propeptide directs chain association during intracellular assembly of the pro-collagen molecule from its three constituent alpha chains. During secretion and deposition as the extracellular matrix, the globular propeptides are cleaved by specific procollagen proteinases, triggering fibril formation, as illustrated in FIG. 1 as reported by M. J. Buehler, Proc Natl Acad Sci US 103, 12285-12290, 2006.

Collagen 1 is a ubiquitous protein in the animal kingdom that evolved to provide a support and framework for cells, and to give strength and resiliency to skin, bone, and tendon. Not unexpectedly, Collagen 1 has been much used as a biomaterial for many medical uses including, skin augmentation, sutures, artificial skins, dura replacements and for other uses. The science of restructuring collagen for use in biomaterials is, however, in its infancy. Much of the research up to now has been characterized by applications of different types of collagen preparations. These experiments have demonstrated that Collagen 1 can be implanted in a variety of sites in the body, and that it doesn't elicit a severe immunologic reaction. Techniques are available for solubilizing large quantities of Collagen 1 from the skin and tendons of a variety of animals or from human skin and for reconstituting the solubilized material into fibrillar form for use in humans.

Professor F. O. Schmitt and his group, working at MIT during the Second World War, investigated the use of collagen sutures and collagen sheets for covering denuded areas of skin. In a remarkable prophetic series of investigations, this group concluded that it was feasible and practical to use collagen sheets and fibers in surgical procedures. They also initiated studies on collagen tubes for nerve repair. Since then, collagen sutures have proved quite successful, with less tissue reaction and better handling properties than catgut.

Collagen 1 can be deposited from solution by a variety of process including casting, lyophilization, electrospinning and other processes well known to one skilled in the art. In most of these procedures, collagen fibers of widely varying diameters and lengths from the micrometer range typical of conventional fibers down to the nanometer range are formed, which provides a mat of interlaced fibers having interstices and pores which provide a suitable foundation for anchoring cells. Owing to their small diameters, electrospun fibers possess very high surface-to-area ratios and are expected to display morphologies and material properties very different from their conventional counterparts occurring in nature. Belamie E. et al. J. Phys. Condens. Matter, 2006, 18, 115-129.

When liquid crystals were discovered in 1888, they quickly became strong candidates for the mechanism by which nature forms living structures from homogeneous multi-chemical mixtures. This is because liquid crystals display a "striking form of self-organization in which directional order appears spontaneously in a homogeneous liquid, not incrementally, as in the growth of crystals layer by layer at the surface, but simultaneously throughout a substantial volume". The organization of structure in a volume is slow if it only occurs through surface apposition of material as with the growth of crystals; while liquid crystals can organize and occur simultaneously over the entire volume.

Liquid crystal is a state of matter that is intermediate between the crystalline solid and the amorphous liquid. There are three basic phases of liquid crystals, known as smectic phase, nematic phase, and cholesteric phase as illustrated in FIGS. 2a-2c. FIG. 2a illustrates the smectic phase in which one-dimensional translational order, as well as orientational order exists. FIG. 2b illustrates the nematic phase in which only a long-range orientational order of the molecular axes exists. Cholesteric phase is also a nematic liquid type with molecular aggregates lie parallel to one another in each plane, but each plane is rotated by a constant angle from the next plane, as shown in FIG. 2c, FIG. 3, and FIGS. 4a-4b. The cholesteric phase is a chiral form of the nematic phase. Chiral describes a structural characteristic of a molecule that prevents it from being superposed upon its mirror image. The "twisted plywood model" shown in FIG. 3 is a model of the organization of molecules in a cholesteric structure. This model explains how typical series of arcing patterns observed in sections of cells and tissues result not from authentic curved filaments but originate from the successive molecular orientations found in the twisted plywood arrangement. The model is constructed as follows. The molecular directions are represented by parallel and equidistant straight lines on a series of rectangles, with the orientation of the lines rotating from one rectangle to the next by a small and constant angle. A periodicity is visible wherein each 180° rotation of the molecular directions corresponds to the half-cholesteric pitch P/2. The rotation is chosen to be left-handed, as has been found in all biological twisted materials studied so far. A cholesteric axis is defined by the left-hand rule, the closed fist of the left hand indicating the progressive direction of twist and the extended thumb of the left hand pointing in the positive direction of the cholesteric axis. Directly visible on the oblique sides of the pyramid are what appear to be superposed series of parallel nested arcs. The concavities of the arcs are reversed on opposite sides of the model. In biological systems this particular geometry has often been described as twisted plywood.

Two major types of twists are found in liquid crystals and their biological analogues and are defined by the disposition of the fibrillar elements either in parallel planes (planar twist) or coaxial cylinders (cylindrical twist) (see FIG. 4). The coaxial cylinders or cylindrical twist are also described as helicoidal. Collagen in the secondary osteons of bone tissue is observed to be in a helicoidal pattern as is cellulose in plant cell walls.

Additional techniques are needed for forming composite collagen-based films. One technique recently reported used an inkjet printer capable of printing at high resolution by ejecting extremely small ink drops. Researchers hope that established printing technology will be able to seed living cells, at micrometer resolution, in arrangements similar to biological tissues. This method was described in Nakamura M. et al., Tissue Engineering, 11:1658-1666 (2005) wherein the authors used a biocompatible inkjet head and investigated a feasibility of microseeding with living cells. Living cells are easily damaged by heat; therefore, they used an electrostatically driven inkjet system that was able to eject ink without generating significant heat. Bovine vascular endothelial cells were prepared and suspended in culture medium, and the cell suspension was used as "ink" and ejected onto culture disks. Microscopic observation showed that the endothelial cells were situated in the ejected dots in the medium, and that the number of cells in each dot was dependent on the concentration of the cell suspension and ejection frequency chosen. After the ejected cells were incubated for a few hours, they adhered to the culture disks. While these developments have been made, this technique is limited and has not found widespread use. This technique is somewhat useful for delivering a material (e.g., cells) to a particular area but it cannot maintain and preserve the material's orientation.

All prior art methods of forming collagen films and matrices to date suffer from limitations as do the collagen-based materials formed there from. The main limitation is to maintain and preserve the native liquid crystal structure of collagen-like materials. For example, electrospinning and casting methods cannot preserve a long-range orientation. Collagen based films and matrices cannot mimic the native semi-crystalline structures of the extra-cellular matrix in the living biological systems. Other methods, like, for example, Langmuir-Blodgett method, have limited orientation and poor repeatability. Accordingly, there is significant need for new collagen-based materials mimicking native structures in living biological systems as well as the reliable and robust methods of producing such materials.

SUMMARY OF THE INVENTION

In general, the present invention is related to collagen compositions and thin films, and to methods of making and using the same. In some embodiments, the present invention is directed to oriented forms of collagen compositions and films such "woven pattern," "basket pattern", "basket weave" or "multi-domain" collagen compositions and thin films, and methods of making.

In some embodiments, the present invention provides at least one monolayer comprised of: a collagen layer, wherein the surface of said collagen layer comprises a multi-domain structure with predominant orientation of rod-like fibers in each of the domains, and pit-like formations at the boundaries of said domains such that the domain orientation changes continuously from one domain to another.

In some embodiments, the present invention provides orientation of the rod-like fibers such that the angle of orientation, or director orientation, varies substantially continuously in a range from 0° to 360° within a domain and from one domain to another. Various director orientations are possible, for example one domain could have a director orientation in the range from 25° to 210° while another domain could have a director orientation in the range from 170° to 5°.

In another aspect, a collagen starting material is provided comprising a solution of nematic collagen wherein the nematic collagen is present at a concentration of 20 mg/ml or higher. Embodiments of the present invention further provide a collagen material comprising: a solution comprising monomeric human or bovine collagen and an acid, for example acetic acid, having a concentration of said collagen in solution of 20 mg/ml or higher. Additionally, in some embodiments the collagen in solution is present as a liquid crystal in a nematic state.

In another aspect, a collagen starting material is provided comprising a solution with a low concentration collagen, for example at a concentration in the range of 1-10 mg/ml, and is concentrated by means such as dialysis or other means known to those skilled in the art to create a nematic collagen solution at a concentration of 20 mg/ml or higher In another aspect, a collagen starting material is provided comprising a solution of nematic collagen and silver nanowires, wherein the nematic collagen is present at a concentration of 20 mg/ml or higher.

In yet another aspect, embodiment of the present invention provides a method of forming a collagen based material. In one exemplary embodiment, methods of forming at least one collagen layer are provided comprising the step of: applying a shear force to a collagen solution at a shear rate of $100~s^{-1}$ and greater. In some embodiments, collagen in the collagen solution is present in a liquid crystal state. In other embodiments, the collagen in solution is present in a nematic liquid crystal state.

In further aspects, a three-dimensional collagen matrix or thin film for use in three-dimensional cell culture is provided by the present invention, said matrix or thin film comprising a collagen layer prepared by shearing and drying on an anisotropic substrate with controlled pre-tilt angle more than two degrees. Additionally, clinical applications of the collagen materials of the present invention are provided.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which:

FIGS. 6A to 6C are AFM images of three collagen-based matrices on substrates made according to the claim 4 of the present invention;

FIG. 7 illustrates an AFM image of a collagen film on glass made according to some embodiments of the present invention;

DETAILED DESCRIPTION OF THE INVENTION

Figure 1:
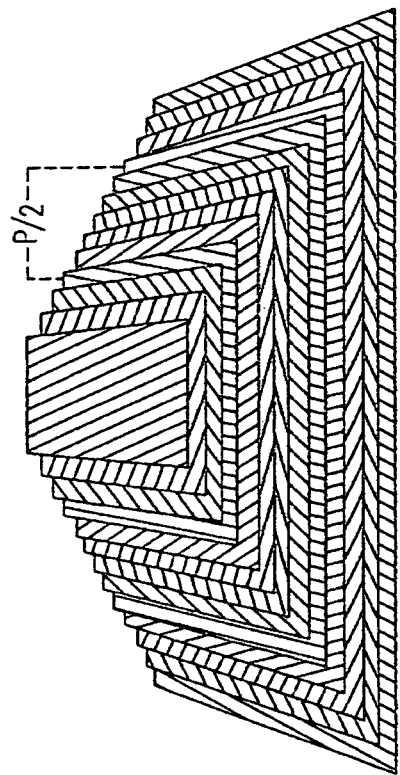
FIG. 1 shows a diagram depicting the known hierarchical design of collagen. The structural features of collagen range from the amino acid sequence, tropocollagen molecules, and collagen fibrils to collagen fibers.
Figure 2:
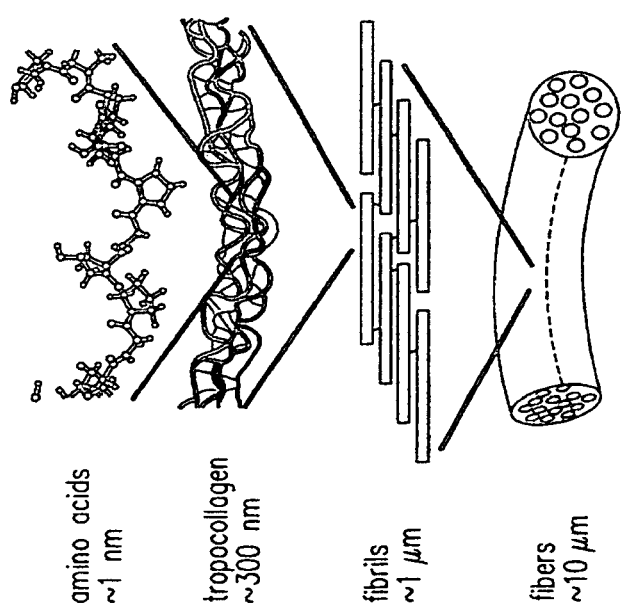
FIGS. 2a-2c are schematic drawings illustrating structures of liquid crystals in smectic, nematic and cholesteric form, respectively, made of rod-like structures such as molecules, microfibrils or fibrils reported in the prior art (A. C. Neville, BioEssays 3: 4-8 (1985))
Figure 3:
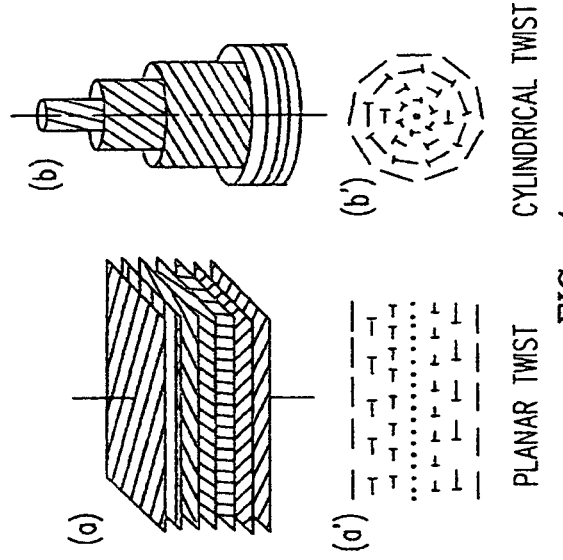
FIG. 3 is a diagram depicting the twisted plywood model as reported by M. M. Giraud-Guille, Int. Rev. Cytol. 166:59-101 (1996)
Figure 4:
FIGS. 4a, 4a', 4b, 4b' depict structures reported by M. M. Giraud-Guille, Int. Rev. Cytol. 166:59-101 (1996) wherein (a) In a planar twist, equidistant straight lines are drawn on horizontal planes, and the direction of the lines rotates regularly from plane to plane. (a') In the conventional notation for a cholesteric geometry applied to a planar twist, lines represent molecules longitudinal to the drawing plane and dots represent molecules perpendicular to it; molecules in oblique position are represented by nails whose points are directed toward the observer. (b) In a cylindrical twist, equidistant helices are drawn on a series of coaxial cylinders, and the angle of the helices rotates regularly from one cylinder to the next. (b') Conventional representation of a cholesteric geometry applied to a cylindrical twist.

It is to be understood that both the foregoing general description and the following detailed description are exemplary and explanatory only and are not restrictive of the compositions, films and methods described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting. The terms "layer" or "film" or "thin film" or "matrix" may be used interchangeably throughout the description. The terms "woven pattern" or "basket pattern" or "basket weave" or "woven collagen" or "multi-domain" may be used interchangeably throughout the description.

In general, embodiments the present invention are related to collagen materials, compositions and films, and to methods of making and using the same. In some embodiments the present invention provides "woven pattern" or "basket pattern" collagen compositions and films, and methods of making. Without limitation, the term "woven" or "basket" pattern collagen as used herein means collagen material or film that is "skin-like" or is a similar representation of the structure of collagen found in human or animal skin. In some embodiments, methods of generating one or more layers or films of collagen on a surface are provided wherein collagen is formed in a substantially uniform manner with a desired orientation on the surface of a substrate.

I. Collagen Compositions, Materials or Films

In one aspect, the present invention provides a monolayer or a multilayer stack comprised of: a collagen material, wherein at least the surface of said collagen material comprises a multi-domain structure with predominant orientation of rod-like fibers in each of the domains, and pit-like formations at the boundaries of said domains such that the director orientation of the domain changes in general continuously within an angular range which at maximum lies between 0° and 360° from one domain to another. In another aspect, the present invention provides a collagen material comprised of a multi-domain structure, each of said domains comprising rod-like fibers, said rod-like fibers exhibiting various orientation defined by one or more directors, and wherein the one or more directors are randomly and substantially uniformly distributed around 360 degrees. Directors may generally characterize the orientation of the fibers along their length or route, whereas the predominant orientation refers to the average orientation within a particular domain. The directors may indicate a contiguous series of domains.

In another aspect, the present invention provides collagen layers or materials with woven patterns, characterized by the presence of vortex-like domains and pores formed by collagen fiber bundles.

Without limitation, FIGS. 5, 6A-6C, 7 and 8A illustrate various embodiments of structures of collagen materials of the present invention. In some embodiments, collagen material or layer 100 comprises fiber bundles 102. By "fiber bundle" here is meant a structure formed by blending and merging of rod-like collagen fibers 103.

Figure 5:
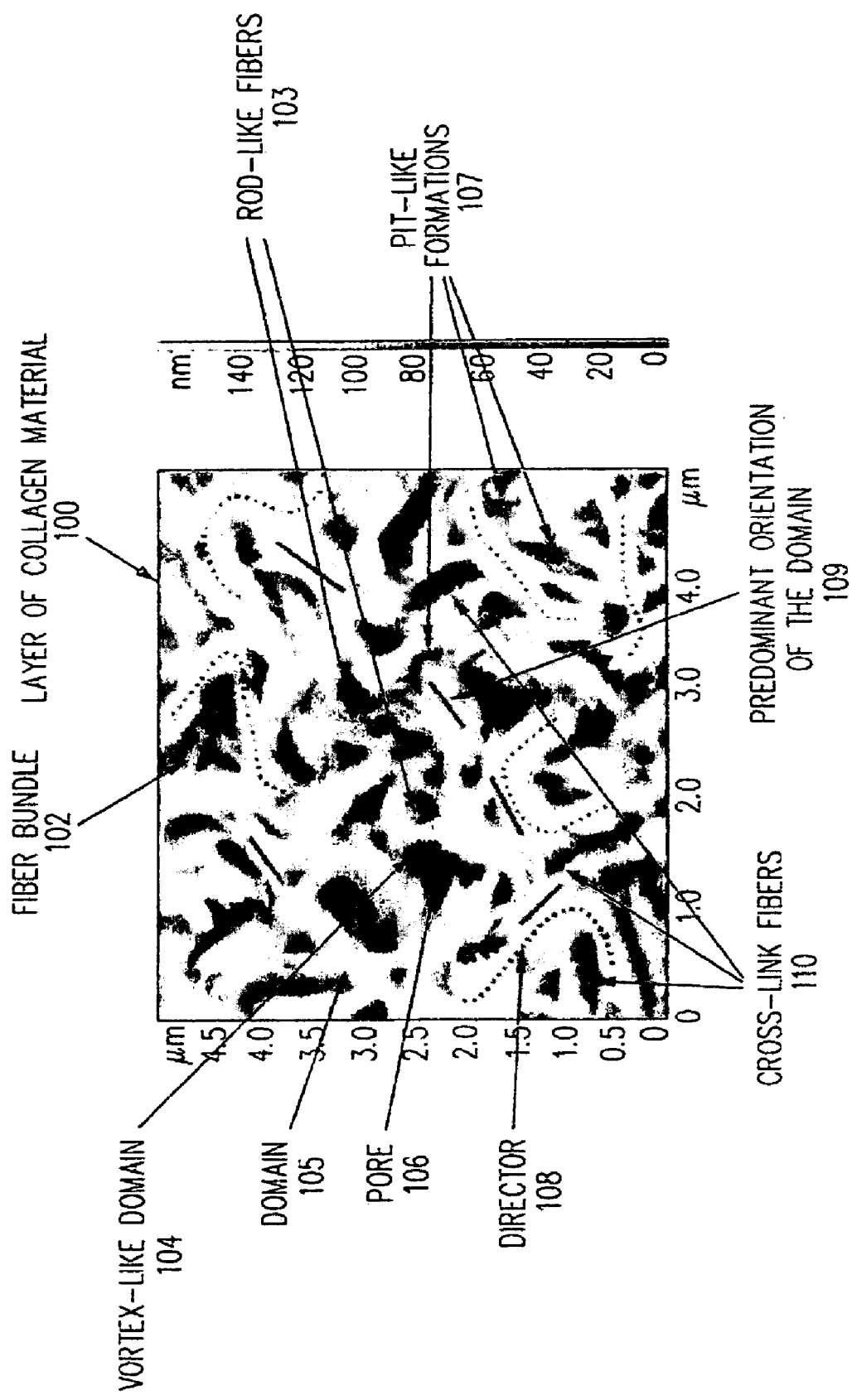
FIG. 5 depicts an AFM image of a collagen layer showing various structural elements of the collagen material and with the definition of terms, according to embodiments of the present invention.

In some embodiments, the fiber bundles 102 form one or more vortex-like domains 104 and pores 106. The collagen material may be viewed as comprising multiple domains 105. By "domain" 105 herein is meant a region of the "rod-like fibers" 103. Domains 105 can also be viewed as a homogenous area bounded or limited by pit-like formations, pores or other defects. In some embodiment the rod-like fibers are aligned in a substantially parallel manner. "Rod-like fibers" 103 blend and merge together to form a "fiber bundle" 102. The fibers within the domain 105 may be further characterized by their directional orientation by one or more directors 108. The "director" 108 is a vector about which the rod-like fibers 103 are preferentially oriented. In some embodiments the one or more directors 108 are randomly and substantially uniformly distributed around 360 degrees. By "vortex-like domains" 104 herein is meant structures formed by contiguous series of multiple domains 105. The collagen layer or material may include pores 106 and/or pit-like formations 107. The pores 106 or pit-like formations 107 may be surrounded by contiguous series of domains. The shape of pores 106 are not limited. In some embodiments the pores 106 exhibit a round or elliptical shape. For example, as discussed in more detail below and as shown in FIG. 5, the pores 106 are the dark areas revealed by atomic force microscope (AFM). In some embodiments, vortex-like domains 104 surround the pores 106. Pit-like formations 107 are typically adjacent the fiber bundles 102, and have a depth that is less than the depth of the pores 106. In some embodiments, each vortex-like domain 104 also has an orientation that can be characterized by a director 108 which changes angular direction as it weaves about the core. The predominant orientation 109 of the domain is the average orientation of the fibers within the domain.

The collagen layer 100 may be comprised cross-linked fibers 110 according to some embodiments of the present invention. By "cross-link fibers" herein is meant fibers 102 that extend almost or substantially orthogonally from a fiber bundle to connect with an adjacent fiber bundle.

Additionally, a collagen material is provided comprised of a multi-domain structure with rod-like fibers oriented almost or substantially parallel to each other within each domain. The domain orientation may change continuously from one domain to another with some exceptions where the domains overlap. The collagen material has pores (or pits), which form the singular areas. These pores induce disclination-like or vortex-like defects in the fibril direction field.

The collagen material or layer may be characterized by the dimension (size) of pores and the distances between the pores. In some embodiments, the maximum length of the pore lies in the range of 50 nm to 5 um and more typically in the range of about 100 nm to 1 um.

The director orientation of the fiber bundles may vary in a random fashion from 0 to 360 degrees throughout the matrix formed by collagen. The wide range of angular director orientation variability is characteristic of the "woven" appearance of the matrix.

In some embodiments, the center to center distance between adjacent pores which lie in the approximate center of the vortex-like domain range from 50 nm to 5 um, more typically in the range of about 200 nm to 1 um.

The center to center distance between cross-link fibers lies in the range of 20 nm to 20 um, and more typically in the range of about 50 to 200 nm.

Of particular advantage, the collagen materials provided by the present invention may further form membranes, films, and mono- or multi-layers comprised of woven pattern collagen material. For example in some embodiments, the collagen material comprises a monolayer or multilayer stack comprises at least one collagen layer as provided herein.

Films and matrices prepared from collagen materials according to embodiments of the present invention are among some of the most interesting materials from both practical and basic research aspects. In one aspect of the present invention biomedical devices are formed from the inventive collagen materials, films and matrices. Additionally, the surface of the collagen materials of the present invention can be studied in a wide variety of ways and modified for particular desired applications.

Collagen membranes for hemodialysis have been prepared by extrusion of a mixture of atelocollagen and dissociated, washed collagen fiber.

All collagen films and membranes age when dried and stored. Drying collapses and condenses the structure, and crosslinks appear over time. Aging can be prevented or slowed by keeping the collagen materials or membranes cold, in the dark, or hydrated.

In another aspect, the collagen-based material provided herein further comprise nanorods, nanowires (for example, carbon nanotubes or silver/gold nanowires), and other additives (for example, sulfonic liquid crystals) to enhance optical and electromagnetic characteristics of the collagen material. Many of these additives can preserve the liquid crystal state of the collagen coating material. A magnetically-guided microfabrication system was recently introduced in R. Valluzzi et al., Philosophical Magazine, 84:3439-3447 (2004), and may be used to attach artificial magnetic particles to the collagen materials of the present invention molecules.

In another aspect, the collagen-based matrices provided herein further can be deposited on the substrate that creates a pretilt angle of the collagen aggregates at the interface. It can be done, for example, by chemical or physical treatment of the substrate before coating. This process is similar to a forming of pretilt angles in liquid crystal display applications.

Collagen films can be made by casting collagen on to methacrylate or other surfaces including glass, other plastics, metals or biological materials. This technique is useful in preparing collagen in a variety of ways for both physical and biological testing, and this type of study should lay the foundation for utilizing collagen as a biomaterial. For example, the ability of a collagen substrate in vitro to support cell attachment, migration and survival, may help in predicting its activities when implanted in vivo.

In some embodiments, collagen materials of the present invention are modified by incorporating hydrogels, peptide-based biomaterials, and other bioactive materials, including but are not limited to, incorporated ligands, encapsulated DNA, and growth factors into the collagen material matrix. For example, proteins such as fibronectin promote cell attachment to collagen. Various synthetic peptides comprising biologically active amino acid sequences can be covalently attached to obtain a desired biological activity. Various proteoglycans will bind tightly to collagen, bind a variety of growth factors and enhance desired biological activities including tissue repair and regeneration.

II. Method of Making

Methods of making collagen matrices, and in particular woven pattern collagen matrices and films are provided. Of particular development, in some embodiments collagen material is produced using a collagen starting material in liquid crystal form. In an illustrative example, collagen-starting material is provided comprising a monomeric human or bovine collagen 1 in an acid solution, for example without limitation an acetic acid solution, wherein the nematic collagen is presented at a concentration of 20 mg/ml or higher. Collagen matrix in many biological systems has a liquid crystal structure. It is the natural state of the collagen, which provides a long-range orientation. Embodiments of the present invention provides for nematic and cholesteric phases of the human Collagen 1 by self-assembly of the monomeric collagen in acidic solution at certain concentration and temperature
(e.g., 20 mg/ml and 6° C.). Of particular advantage the inventive methods and compositions promote maintaining and preserving the native liquid crystal structure of collagen-like materials.

In some embodiments, the liquid crystal state of the collagen is selectively controlled. Selective control can be achieved by a variety of methods, including but not limited to:

observation of typical pattern in the material between crossed polarizes with and without staining or/and retardation enhancement; polarized microscopy with and without staining or/and retardation enhancement; Mueller matrix measurements, and polarimetry (i.e., Axometrics polarimeter). It has been shown that high concentrations (5-30 mg/ml) of procollagen molecules in physiological buffer develop long range nematic and precholesteric liquid crystal ordering extending over 100 $\mu m^2$ domains, while remaining in solution (R. Martin et al., J. Mol. Biol. 301: 11-17 (2000)). Procollagen concentrations in vivo are estimated at several tens of milligrams per milliliter in the secretory vesicles and the molecules are often observed to be aligned in a nematic-like ordering.

In some embodiments, the collagen is concentrated by various methods known in the art, including but is not limited to filtration, rotary evaporation, and dialysis membrane.

In another embodiment, the collagen material may be prepared by ultrasonic treatment. Brown E. M. et al. Journal of American Leather Chemists Association, 101:274-283 (2006), herein is incorporated by reference by its entirety.

There are numerous ways to achieve such deposits depending on the surface to be coated, the area to be coated and the homogeneity desired.

In some embodiments, the woven pattern collagen layer is produced by extrusion of collagen solutions from a capillary or a needle onto a flat surface under shear which can provide homogeneity in the shearing direction. However, in some embodiments, this method is not preferred because there is a high variation in the coating across the shearing direction such that only small area of the woven like pattern collagen can be made with low reproducibility and the control of thickness and other parameters, as is the area of application.

Collagen layers provided herein may be produced by slot die technology. In one example, slot die technology as described in Chang Y R et al., Journal of Colloid and Interface Science 308:222-230 (2007), Paukshto M., et al., Journal of the SID 13:765-772 (2005); Fenell, L., et al., Asian Display/IDW '01:601-603, and U.S. Pat. Nos. 4,299,789, 4,869,200 and 6,174,394, all expressly incorporated by reference in their entireties, may be employed.

Of particular advantage, in one embodiment collagen layers are produced by application of a shearing force. This inventive method allows for specific arrangement of the collagen fibrils and promotes the formation of selective patterns in the resultant collagen matrices and films. The inventive method maintains and preserves the native phase of the collagen-based materials. In an illustrative embodiment, methods of forming at least one collagen layer are provided comprising the step of applying a shear force to a collagen solution at a shear rate of 100 mm/sec and greater. In some embodiments, the collagen solution is present in a liquid crystal state. In another embodiment, the collagen solution is present in a nematic liquid crystal state at a concentration of 20 mg/ml or higher.

The shear force may be applied to the collagen solution by any suitable means. In one non-limiting example, the shear force is applied using a slot die tool, operated under pressure. The collagen solution may adjusted for concentration, pH, salt constituents and other factors and before being forced through the slot die under pressure onto clean desired surface, such of glass, plastic or other substrate material. The application process may be computer controlled to assure homogeneity of coating, depth of deposit and other desired parameters.

In another non-limiting example, the shear force is applied using a liquid film applicator assembly described in patent application "A Liquid Film Applicator Assembly and Rectilinear Shearing System Incorporating the Same" filed Nov. 20, 2007 by D. McMurtry, M. Paukshto and Y. Bobrov, the entire disclosure of which is hereby incorporated by reference.

In another non-limiting example, the shear force is applied using two substantially parallel plates of suitably smooth material such as glass. The collagen material is deposited on the first plate. The second plate is placed on top of the first plate creating a "sandwich". A suitable force is applied to squeeze the two plates together to create a small gap between them. The first plate is translated relative to the second plate to create the shear force on the entrapped collagen material. The plates may be flat or planar. Alternatively, the plates may be curved have some other non-planar topography.

The main method parameters, which influence the collagen orientation, are: shearing force speed, coating gap, shearing plate smoothness, shearing plate surface energy, collagen concentration and additives, relative humidity and temperature, drying speed, and surface pretreatment. In general and without limitation, shearing speed in typically in the range of up to 1000 mm/sec, more particularly in the range of about 20 mm/sec to 100 mm/sec. As the shearing force is applied at a particular speed, collagen material flows onto the substrate to be coated through a coating gap and along the length of a shearing zone. In general and without limitation, the coating gap is in a range of 1 $\mu$m-50 $\mu$m, and more particularly in the range of 5 um to 30 $\mu$m. The shearing zone is preferably relatively long, for example the shearing zone may have a length of up to 30 mm. It will be understood to those of skilled in the art that other process parameters may be selected based on the teaching of the present invention by applying routine experimentation. For example, the collagen structures shown in FIGS. 6A and 6B were made at two different coating speeds (20 mm/sec and 60 mm/sec, respectively) with coating gap of 5 $\mu$m.

The methods provided herein allows the achievement of a variety of orientation patterns (see, for example, FIGS. 6A-6C) by a relatively inexpensive shearing method with extremely low material consumption, which is important when using unique biomaterials. Moreover methods result in highly oriented structures produced by high shearing speed (up to 1000 mm per second) with long length of shearing zone (up to 30 mm) and precisely controlled gap within the range 1 $\mu$m-50 $\mu$m. In addition it is possible to control the alignment and drying during coating process.

In some embodiments, the collagen layers provided herein are formed on top of an anisotropic layer with the anisotropy axis. For example, the structure in FIG. 6C was formed atop of an anisotropic layer with the anisotropy axis parallel to the coating direction.

An examination of the resultant collagen orientation reveals that one can always see a multidomain structure with rod-like fibers oriented parallel to each other within every domain. Moreover the domain orientation changes continuously within an angular range which at maximum lies between 0° and 360° from one domain to another. The structure has pores (or pits) which appear as black colored singular areas. These pores induce disclination-like or vortex-like defects in the direction field of the fibrils.

In some embodiments, the method provided herein is used for the fabrication of a multilayer structure by sequential coatings. This multilayer structure may have different functional layers including a collagen layer. The property of the first layer on the substrate can be chosen to enable easy delamination of the whole structure.

In yet additional embodiments, woven pattern collagen materials and layers are formed by non-contact slot-die type methods according to the present invention. In this embodiment, methods are characterized by any one of more of: (1) high shearing speed; (2) high fluid material consumption of a starting collagen solution in order to fill the die cavity and pump with collagen solution (3) controlled gap distance; (4) long length of shearing zone; and/or (5) in-situ control of alignment and drying.

Without limitation in some embodiments, the shearing is speed is in the range of 10 to 100 mm per sec, more typically in the range of 20 to 60 mm per sec, and up to 1000 mm per sec. The fluid material consumption is in the range of 0.5 cc to 2 liters, more typically 0.5 cc to 2 cc. The gap distance is generally in the range of 1 to 50 um, and more typically in the range of 5 um to 30 um. The shearing zone has a length generally in the range of up to 30 mm, more typically in the range of 1 mm to 10 mm.

In some embodiments, the alignment and drying during coating process are controlled by a surface rubbing and air knife using nitrogen at the temperature in the range of 4° C. to 37° C., more typically 6° C. to 25° C.

Then the sample was measured by AFM and the results are shown at FIGS. 6a to 6c. The same measurements were repeated a month later, and the same output was observed.

Of particular advantage, this coating method of the invention presents the opportunity for multilayer roll-to-roll coating of biological materials on flexible substrates. This provides the opportunity for large volume production of biological materials on a scale not before enable, due in part because this embodiment of the method is a non-contact coating method, providing high alignment to lyotropic liquid crystals with very low fluid material consumption; and capable of a high level of uniformity.

Figure 8A:
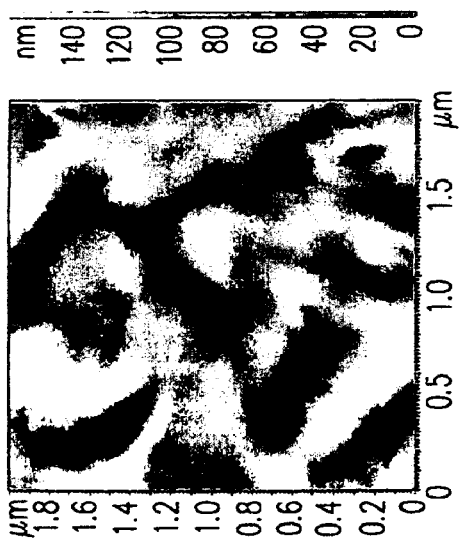
FIGS. 8A and 8B are AFM images of a collagen monolayer coated on glass according to embodiments of the present invention.
Figure 8B:
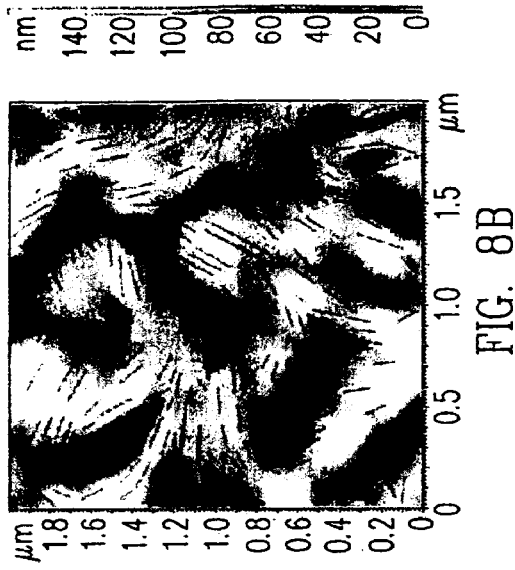
Figure 9:
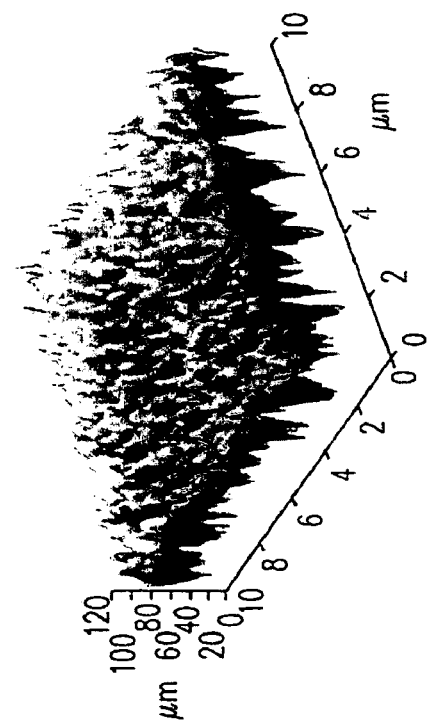
FIG. 9 is a 3-dimensional collagen matrix having AFM scan of 512×512 points in the area of 5μ*5μ, and wherein the average pit's depth is 120 nm, according to embodiments of the present invention.

This method allows the achievement of a variety of collagen orientation patterns see, for example, FIGS. 6A-6C and, FIGS. 7-9. The typical broadtail (caracultcha) like pattern is shown at the FIG. 7. It has very typical non-symmetrical histogram with zero mean value standard deviation 254 A.

if the profile of the coated collagen sample is measured within a representative area (for example 10 µm*10 µm) then a mean level of this profile can be always defined to be equal zero. Now one can obtain the height distribution function, J. M. Bennett and L. Mattson, Introduction to Surface Roughness and Scattering, OSA, Washington, D.C., 1999, 130p, (also called an amplitude density function).

Collagen based samples coated by methods of the present invention have non-symmetrical height distribution function of the surface profile. This type distribution was compared with normal distribution. The normal distribution has the same mean value (which is zero) and same rms value (see, for example, J. M. Bennett and L. Mattson, Introduction to Surface Roughness and Scattering, OSA, Washington, D.C., 1999, 130p).

In some embodiments, the collagen layer provided herein can be produced by combining different deposition methods, such as by combining slot-dye and then jet printing and patterning.

III. Applications

Solubilized, purified and reconstituted into oriented collagen materials and fibers of the present invention find use in many applications.

A. Cell Culture

In one aspect, the present invention provides woven pattern collagen materials and films that find uses in cell cultures.

Collagen as a film or as a coating on other materials has also been used in tissue culture for the growth of fastidious cells. The protein surface and the orientation of the fibers appear to promote cell growth in vitro and probably in vivo as well.

By "cell culture" or "culture" herein is meant the maintenance of cells in an artificial, e.g., an in vitro environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

By "cultivation" herein is meant to the maintenance of cells in an artificial environment under conditions favoring their proliferation, differentiation, production of specific proteins both recombinant and natural or continued viability, in an active or quiescent state. Thus, "cultivation" may be used interchangeably with "cell culture" or any of its synonyms described above.

Generally, cell culture is carried out by growing cells in a culture vessel in the presence of cell culture medium. By "culture vessel" herein is meant a glass, plastic, or metal container and the like that can provide an aseptic environment for culturing cells. Culture vessels include but are not limited to petri dishes and 96-well plates.

In some embodiments, the woven collagen layer is used to coat the surface of a cell culture vessel.

The use of various biological macromolecules as coating for has been widely employed in tissue culture as have their use in coating medical devices. Such biological materials include collagen, gelatin, fibronectin, fibrin, heparin and other factors. When used as coatings, these factors support better biocompatibility and include in the case of tissue culture to enhance the attachment, survival, growth, migration and differentiation of cells added to the dish. Current concepts suggest that such coatings bind to receptors on the surface of the cells which then support the attachment multiplication and behavior of the cells. Such surfaces prepared using current methods are not necessarily homogeneous in terms of completeness of the coating. More over the structure that collagen, for example, which assumes on the dish in no way corresponds to the arrangement of collagen in the native tissues but is largely random.

The surfaces on which cells grow play a key role in controlling cellular behavior. Spradling A., et al., Nature; 414: 98-104 (2001); Streuli C. Curr Opin Cell Biol; 11 (5): 634-40 (1999). Properties such as surface roughness, hydrophobicity, and specific interaction with the cell surface can all affect cell activity. Saltzman W M. Cell Interactions with Polymers. In: Lanza R P, Langer R S, Vacanti J, and editors. Principles of Tissue Engineering. 2nd ed. San Diego: Academic Press; 221-35 (2000). The modulation of cell activity through substrate interaction can have a significant effect on biomaterial-based therapies. Tissue engineered constructs, ex-vivo cell propagation, and cell encapsulation all require some type of interaction between cells and supporting material for growth, function, and/or delivery. Lanza R P, Langer R S, Vacanti J. Principles of Tissue Engineering. 2nd ed. San Diego: Academic Press; 2000. The modulation of bioactivity through the rational design of materials has been widely investigated. Hubbell J A., Curr Opin Biotechnol 1999; 10 (2): 123-9. One example includes hydrogels that can enhance cellular growth through incorporation of tethered adhesive ligands. Lutolf M P., et al., Nat Biotechnol 21:513-8 (2003). Material-based control of cellular function is a potentially powerful tool for controlling stem cells, which have the potential to differentiate into many tissue types. For example, a self-assembling peptide based biomaterial that can specifically direct the differentiation of neural progenitor into neurons was recently described by Silva G A., et al., Science 303:1352-5 (2004). Much research is currently focused on the development of bioactive materials through the incorporation of ligands, and encapsulation of DNA and growth factors Chen R R and Mooney D J. Pharmaceutical Research 20:1103-12 (2003); Sakiyama-Elbert S E and Hubbell J A. Ann Rev Mater Res; 31:183-201 (2001).

In some embodiments, the cells contact the cell culture medium. By "cell culture medium," "culture medium" (plural "media" in each case) and "medium formulation" herein is meant to a nutritive solution that supports the cultivation and/or growth of cells; these phrases may be used interchangeably.

By "contacting" herein is meant the placing of cells to be cultivated into a culture vessel with the medium in which the cells are to be cultivated. The term "contacting" encompasses inter alias mixing cells with medium, perfusing cells with medium, pipetting medium onto cells in a culture vessel, and submerging cells in culture medium.

There are many varied types of cell culture media that can be used to support cell viability, for example DMEM medium (H. J. Morton, In Vitro, 6, 89/1970), F12 medium (R. G. Ham, Proc. Natl. Acad. Sci. USA, 53, 288/1965) and RPMI 1640 medium (J. W. Goding, J. Immunol. Methods, 39, 285/1980; JAMA 199, 519/1957). Such media (often called "basal media"), however, are usually seriously deficient in the nutritional content required by most animal cells. Often, serum must be added to the basal media to overcome these deficiencies. Generally, fetal bovine serum (FBS), horse serum or human serum is used in significant concentrations.

While the use of FBS is desirable, and often necessary, for proper cell growth, it has several disadvantages. It is relatively expensive, and its use greatly increases the cost of cell culture. In addition, it is difficult to obtain serum with consistent growth characteristics. Further, the biochemical complexity of FBS can complicate the downstream processing of the proteins of interest, therefore raising the production costs.

Serum-free medium is an excellent alternative to standard serum-containing media for the cultivation of cells. It has several advantages, which include better definition of the composition, reduced contamination and lower cost. A serum-free medium having cultivation ability comparable to that of the conventional serum-containing medium has long been sought.

One strategy to develop serum-free media has been to supplement the basal media with appropriate nutrients to avoid the addition of FBS, without sacrificing cell growth and/or protein production. Examples of such components include bovine serum albumin (BSA) or human serum albumin (HSA); certain growth factors derived from natural (animal) or recombinant sources, including epidermal growth factor (EGF) or fibroblast growth factor (FGF); lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements. See Cell Culture Methods for Molecular and Cell Biology, Vol. 1, Barnes, D. W., et al., eds., New York: Alan R. Liss, Inc., (1984), herein incorporated by reference in its entirety.

B. Scaffolds with Oriented Collagen

In another aspect, the present invention provides scaffolds with oriented collagen, such as scaffolds with woven pattern collagen materials formed thereon.

In some embodiments, woven pattern collagen layers of the present invention are used in cell culture to provide a platform or guidance for growing cells and optionally may increase their proliferation rate. There is a strong evidence that oriented collagen layer provide a guidance for growing cells and increase their proliferation rate. In the paper Yoshizato K. et al., Growth and Differ., 23 (2), 175-184 (1981), a collagen film in which the collagen fibers were aligned was prepared and characterized by scanning electron microscopy. Cell orientation on this film was studied in vitro using human fibroblasts and chick embryo myoblasts. Ninety-four percent of innoculated fibroblasts were aligned along the direction of the collagen fiber. The myoblasts showed a similar alignment along the direction of collagen fiber. Myoblast fusion was accelerated on the aligned membrane as compared to a randomly oriented film, suggesting some role of contact guidance in muscle cell differentiation.

Figure 10:
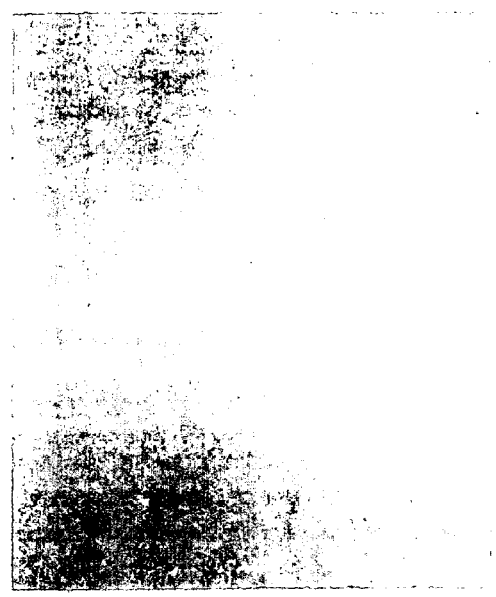
FIG. 10 is an image of human fibroblast cells growing on a collagen matrix made according to certain embodiments of the present invention.

Additionally, the invention provides a scaffold or layer with woven pattern collagen layer(s) formed thereon for growing stem cell. FIG. 10 shows stem cells growing on a coated collagen layer formed according to the present invention. A high rate of proliferation of stem cells was demonstrated.

In some embodiments, the oriented collagen is used in a would healing process. During the wound healing process, oriented collagen acts to modulate cell proliferation and migration and is important in the wound contraction process. Cuttle L., et al., Wound Repair and Regeneration, 13:198-204 (2005). The patterns of collagen deposition in healing fetal and adult wounds differ markedly. Fetal skin regenerates collagen fibers in neat, well-organized patterns with close to perfect tissue architecture, whereas postnatal and adult skin heals with collagen laid down in thick disorganized patterns and scar formation. Colwell A S et al., Front Biosci; 8:s1240-8 (2003). The scarless healing properties of fetal skin are lost in many animal models in late gestation. Further evidence of importance of collagen structure for scarless wound healing was presented in Goffin, A J., et al., Oriented Collagen Films for Wound-Healing Applications, 2006, Annual Meeting, Society for Biological Engineering.

In some embodiments, the oriented collagen provided herein is used in tissue, engineering. Different forms of collagen are the most important materials of tissue engineering. They are widely used for healing of burn wounds, artificial nerve construction, regeneration of damaged heart tissue, etc. Since the extra cellular matrix of the human body has a well oriented structure which changes with age and human condition, G. Avtandilov et al., Journal of Applied Crystallography, 33:511-514 (2000); P. Lazarev et al., Annual International Conference of the IEEE Engineering in Medicine and Biology—Proceedings; 2000; v. 4, p. 3230-3233; Cuttle, L et al., Wound Repair and Regeneration, 13:198-204 (2005), researchers have tried to mimic this structure. Substantial effort has been spent to achieve the desired orientation of collagen fibrils by mechanical uniaxial stretching, by use of microgroove and other microstructured substrates, by use of shear flow orientation, etc.

C. Collagen Clinical Applications

In one aspect, the present invention provides clinical applications using woven pattern collagen materials of the present invention.

The preparation of collagen for use as a biomaterial can be broadly classified into two major approaches. In one approach, biological structures are treated in some way to remove noncollagenous materials and to strengthen the remaining collagen. Existing structure, and probably many of the intermolecular crosslinkages, are retained. In the second approach, collagen is first solubilized and purified, and then attempts are made to re-form and re-crosslink the material in the proper shape. The former approach has the advantage of exploiting normal, biological, three-dimensional structure in a biomaterial, but has the disadvantage of having relatively fixed, and predetermined configurations. The latter approach has had the problem of reconstituting collagen materials with appropriate strength, but offers a very broad potential in possible applications.

The success of collagen heterografts indicates, among other things, that clinically significant antigenicity is generally not a problem. One of the most completely studied structures has been the collagen arterial graft of bovine origin, produced by Johnson and Johnson.

Reconstituted collagen would seem to have a greater potential for biomaterials. Reconstituted collagen can be purified, its structure defined, side groups altered, and any type of biomedical device designed. The major medical applications to date have been extruded collagen fibers, collagen membranes, collagen gels, and collagen sponges.

In some embodiments, the collagen films provided herein are used to prevent adhesions following tendon injuries, to lengthen levator palpebrae muscles ophthalmic surgery, and to repair transected nerves. Aparray & Tanner reported the successful use of collagen film in treating corneal burns. Prudden & Wolarsky have used collagen prepared from enzyme-treated bovine cartilage to enhance wound healing. They found that this preparation reversed steroid induced inhibition of wound healing.

Collagen films provided herein may further are used for burn dressings and wound healing. In some embodiments, the collagen is preferably not heavily cross-linked. If the films are heavily cross-linked, they do not become incorporated into the tissue, but rather, granulation, and re-epithelialization take place beneath the films. Here the film acts as an inert dressing. Collagen felt or sponge, on the other hand, may function as a true artificial skin. Healing of bone defects and wounds also appears enhanced by collagen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

The following examples are provided for illustration purposes only, and are not intended to limit the scope of the present invention in any way.

The woven pattern of collagen can be characterized quantatively by the size of the pores and the distance between the pores. Four photos shown in FIGS. 11A-11D were characterized using the measurement features of AutoCAD. The results are shown in the following tables. It is to be understood that other techniques for characterizing the collagen materials of the present invention may be employed, and that the following data and results are provided for illustration purposes only and are not intended, to limit the scope of the invention in any way.

Figure 11B:
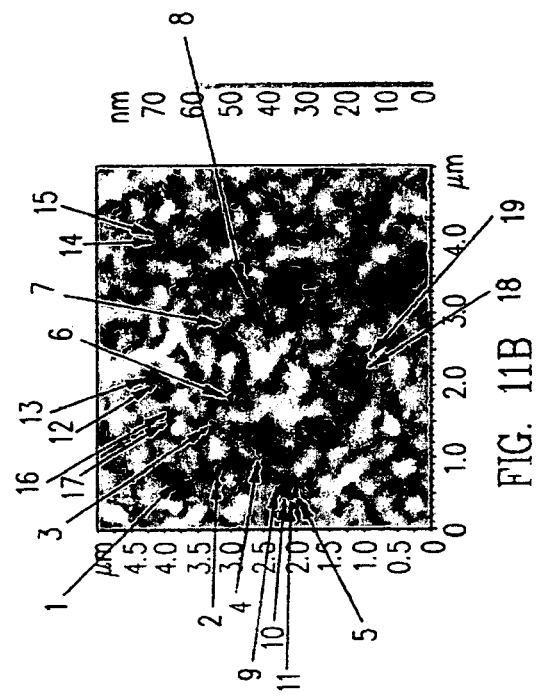
FIGS. 11A-11D are AFM images of collagen layers with pores identified in each of the collagen materials, according to embodiments of the present invention.
Figure 11D:
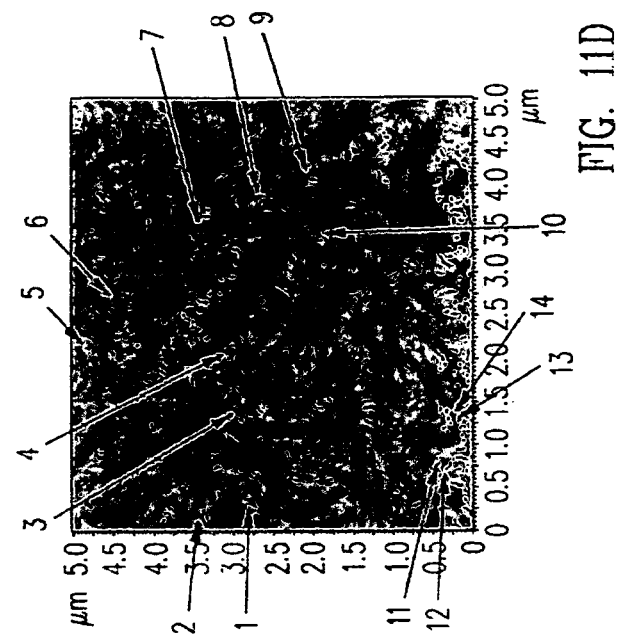
Figure 11A:
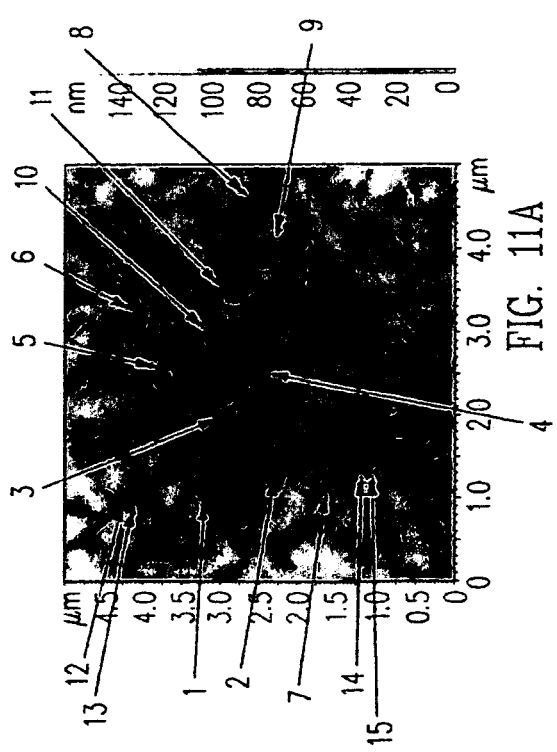

Referring to FIG. 11A measurements were taken at 11 points at various locations across the collagen film. Ellipses were drawn around each of the pores to create an approximate boundary. The major and minor axes of these ellipses were noted. Table 1 shows the measurement results of FIG. 11A directed to the dimensions of the elliptical pore shape.

TABLE 1

Dimensions of elliptical pore shape

| POINT | MAJ (nm) | MIN (nm) | RATIO |
|---|---|---|---|
| 1 | 420 | 245 | 1.7 |
| 2 | 508 | 280 | 1.8 |
| 3 | 438 | 210 | 2.1 |
| 4 | 315 | 210 | 1.5 |
| 5 | 315 | 158 | 2.0 |
| 6 | 385 | 140 | 2.8 |
| 7 | 263 | 140 | 1.9 |
| 8 | 858 | 245 | 3.5 |
| 9 | 508 | 298 | 1.7 |
| 10 | 420 | 193 | 2.2 |
| 11 | 438 | 193 | 2.3 |
| avg | 442 | 210 | |
| std dev | 158 | 53 | |

Next, to determine typical pore-to-pore separations, the distance from the center of the ellipse surrounding one pore was measured to the center of the ellipse surrounding an adjacent pore.

TABLE 2

Typical C-C Pore dimensions

| Point-to-point distance | AFM (nm) |
|---|---|
| 1-2 | 998 |
| 2-3 | 945 |
| 3-1 | 998 |
| 3-4 | 665 |
| 5-6 | 770 |
| 2-7 | 665 |
| 8-9 | 683 |
| 10-11 | 595 |
| avg | 790 |
| std dev | 165 |

The typical spacing of several cross link fibers was measured and the results are shown in Table 3 below

TABLE 3

Cross-link fiber spacings

| Spacing | nm |
|---|---|
| 12-13 | 140 |
| 14-15 | 123 |
| avg | 131 |

Tables 4-6 shows the measurement results of FIG. 11B using the same methodology as described above for FIG. 11A.

TABLE 4

Dimensions of elliptical pore shape

| POINT | MAJ nm | MIN nm | RATIO |
|---|---|---|---|
| 1 | 245 | 142 | 1.7 |
| 2 | 336 | 116 | 2.9 |
| 3 | 168 | 129 | 1.3 |

TABLE 4-continued

Dimensions of elliptical pore shape

| POINT | MAJ nm | MIN nm | RATIO |
|---|---|---|---|
| 4 | 207 | 181 | 1.1 |
| 5 | 155 | 129 | 1.2 |
| 6 | 168 | 129 | 1.3 |
| 7 | 194 | 103 | 1.9 |
| 8 | 220 | 129 | 1.7 |
| avg | 212 | 132 | |
| std dev | 59 | 23 | |

TABLE 5

C-C Pore dimensions

| Point-to-point distance | AFM (nm) |
|---|---|
| 1-2 | 646 |
| 2-3 | 633 |
| 3-1 | 917 |
| 2-4 | 698 |
| 3-4 | 762 |
| 4-5 | 801 |
| 3-6 | 465 |
| 7-8 | 607 |
| avg | 691 |
| std dev | 137 |

TABLE 6

Cross-link fiber spacings

| Point-to-point distance | AFM (nm) |
|---|---|
| 9-10 | 103 |
| 10-11 | 78 |
| 12-13 | 116 |
| 14-15 | 103 |
| 16-17 | 103 |
| 18-19 | 103 |
| avg | 101 |
| std dev | 13 |

Figure 11C:
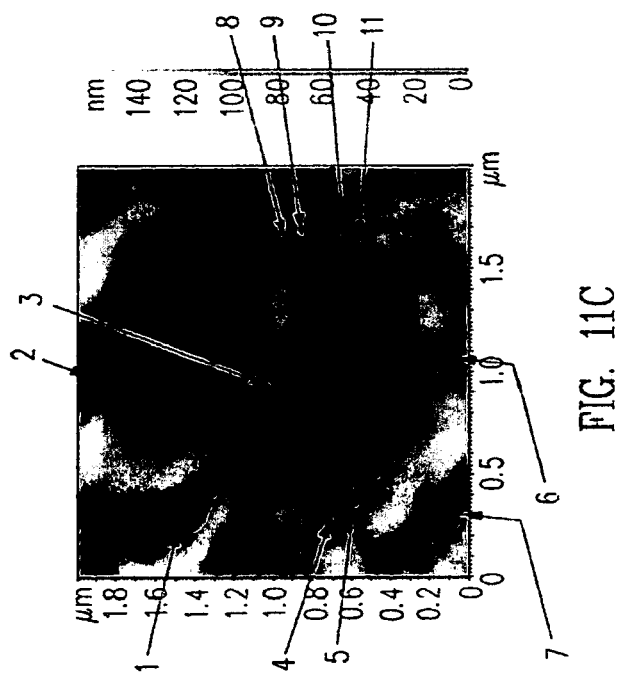

Tables 7-9 show the measurement results of FIG. 11C using the same methodology as described above for FIG. 11A.

TABLE 7

Dimensions of elliptical pore shape

| POINT | MAJ nm | MIN nm | RATIO |
|---|---|---|---|
| 1 | 575 | 226 | 2.5 |
| 2 | 265 | 207 | 1.3 |
| 3 | 155 | 149 | 1.0 |
| 4 | 187 | 110 | 1.7 |
| 5 | 174 | 110 | 1.6 |
| 6 | 268 | 136 | 2.0 |
| 7 | 123 | 123 | 1.0 |
| avg | 250 | 151 | |
| std dev | 153 | 47 | |

TABLE 8

C-C Pore dimensions

| Point-to-point distance | AFM (nm) |
|---|---|
| 1-2 | 824 |
| 2-3 | 1056 |
| 3-1 | 849 |
| 3-4 | 585 |
| 4-7 | 581 |
| 7-6 | 778 |
| 6-3 | 753 |
| 4-5 | 191 |
| avg | 702 |
| std dev | 256 |

TABLE 9

Cross-link fiber spacings

| Point-to-point distance | AFM (nm) |
|---|---|
| 8-9 | 90 |
| 10-11 | 87 |
| avg | 89 |

Tables 10-12 show the measurement results of FIG. 11D using the same methodology as described above for FIG. 11A.

TABLE 10

Dimensions of circular pore shape

| POINT | DIAM (nm) |
|---|---|
| 1 | 193 |
| 2 | 203 |
| 3 | 203 |
| 4 | 166 |
| 5 | 101 |
| 6 | 157 |
| 7 | 166 |
| 8 | 212 |
| 9 | 203 |
| 10 | 249 |
| avg | 185 |
| std dev | 40 |

TABLE 11

C-C Pore dimensions

| Point-to-point distance | AFM (nm) |
|---|---|
| 1-2 | 635 |
| 3-4 | 645 |
| 5-6 | 672 |
| 7-8 | 847 |
| 8-9 | 562 |
| 9-10 | 672 |
| avg | 672 |
| std dev | 95 |

TABLE 12

Cross-link fiber spacings

| Point-to-point distance | AFM (nm) |
|---|---|
| 11-12 | 64 |
| 13-14 | 64 |
| avg | 64 |

Table 13 summary the measurement results of FIGS. 11A-D.

TABLE 13

Data summary

| | PORE SHAPE (Major elliptical axis or circle diameter) (nm) | C-C PORE DIST (nm) | CROSS LINK FIBER SPACINGS (nm) |
|---|---|---|---|
| FIG. 15A | 442 | 790 | 131 |
| FIG. 15B | 212 | 691 | 101 |
| FIG. 15C | 250 | 702 | 89 |
| FIG. 15D | 185 | 672 | 64 |
| avg | 272 | 714 | 96 |

Figure 12A:
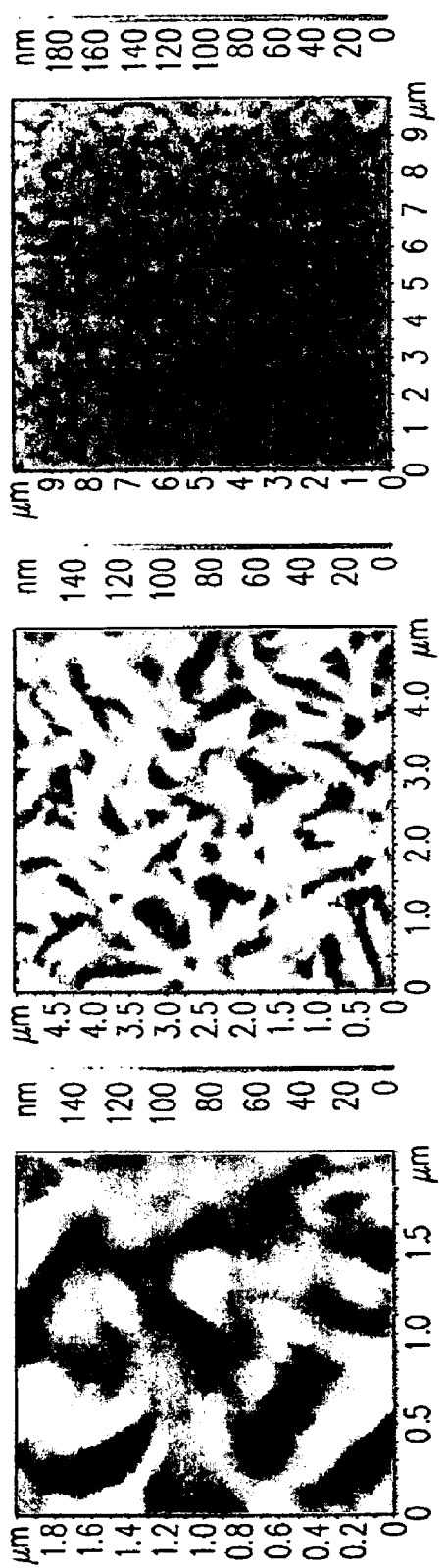
FIGS. 12A-12C show AFM images of collagen layers, histograms and associated data, respectively for three collagen materials illustrating their topography characteristics.
Figure 12B:
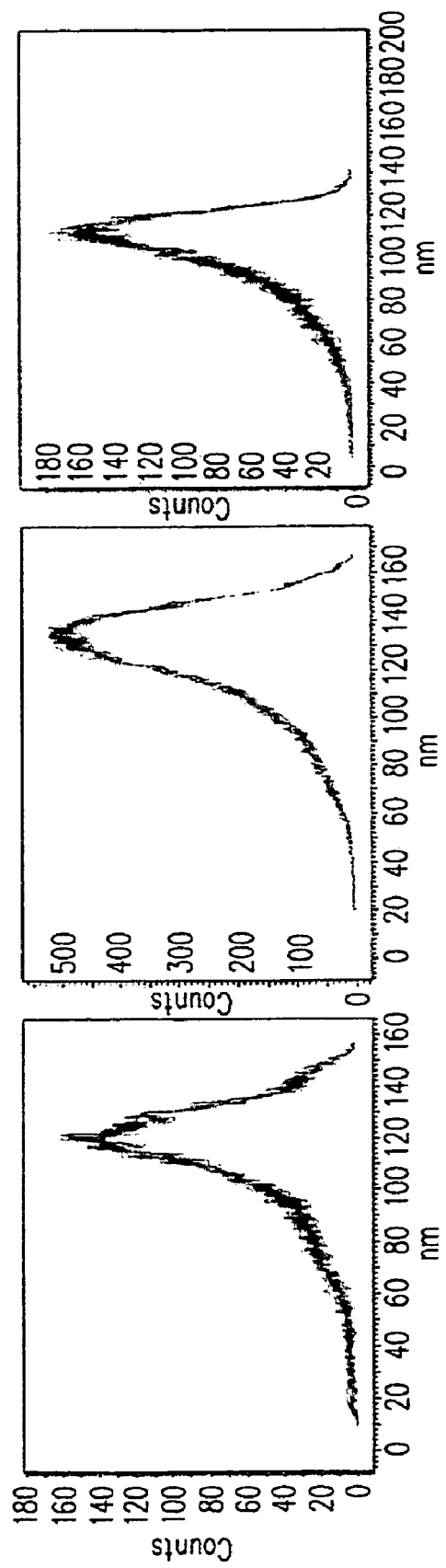
Figures 12C, 13:
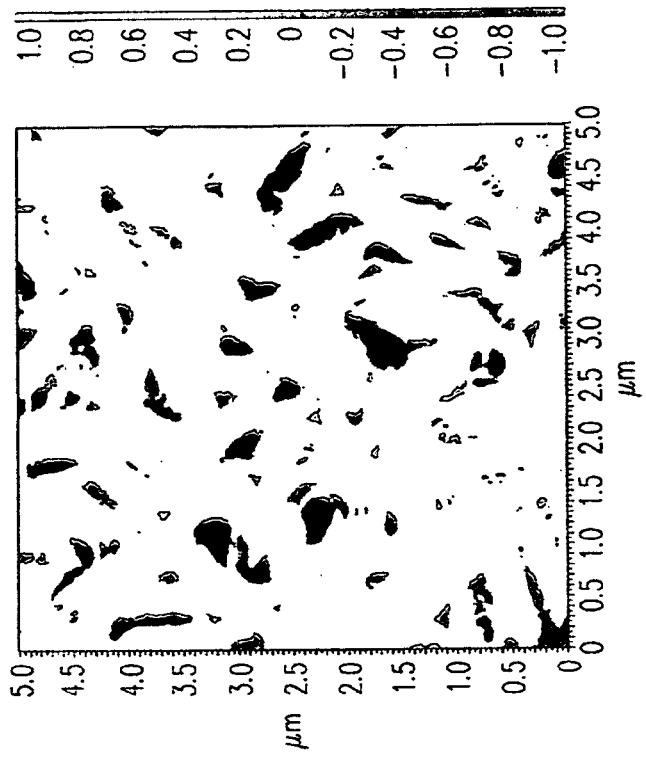
FIG. 13 is a shadow AFM image of a collagen layer formed according to embodiments of the present invention, illustrating pore size characterization.

Referring to FIGS. 12a-12c, the topography of collagen materials formed by the present invention are further characterized. Specifically, height distribution of collagen film topography generally characterizes the collagen surface structure. Averaged collagen pore size is proportional to surface statistic parameters Sa (average roughness) or Sq (RMS roughness). The topography can be evaluated as 2*Sa or 2*Sq. FIGS. 12a-12c show AFM images of collagen layers, histograms and associated data, respectively for three collagen materials of the present invention illustrating their topography characteristics.

Pore sizes were also characterized as shown with reference to FIG. 13. To characterize pore size and bundle width an AFM topography image is used as shown in FIG. 13. To estimate the topography, a mask of the cross section is formed. The level of topography cross section was chosen at 50% from maximal topography height. Pore size is measured as averaged size along the greatest and shortest axes with consecutive averaging over all pores in the image. The bundle size is measured as distance between the nearest edges of two nearest pores with consecutive averaging over all measured values.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

What is claimed is:

1. A monolayer or multilayer stack comprising a collagen layer, wherein a surface of said collagen layer comprises:
    a plurality of domains with predominant orientation of rod-like fibers in each of the domains, and
    a plurality of pit-like formations at the boundaries of said domains such that the domain orientation changes substantially continuously from one domain to another.

2. The monolayer or multilayer stack according to claim 1, wherein said collagen layer is formed by applying shear to a collagen solution at a shear rate of 100 s$^{-1}$ or higher.

3. The monolayer or multilayer stack according to claim 1, wherein said collagen layer is formed by a slot-die type system from liquid phase at a shear rate of 1000 s$^{-1}$ or higher.

4. The monolayer or multilayer stack according to claim 1, wherein said collagen layer is made by a liquid film applicator comprising:
    (i) at least two longitudinal side members having the form of parallel wedge-like rails with their bases occurring in the same plane as the substrate;
    (ii) a crossover member having the form of a bridge between said side members, wherein said crossover member has at least one flat face and is in contact with each said rail in at least one point; and
    (iii) a clamp system ensuring strict fixation of the bridge at any preset position on said rails, wherein said bridge can be moved along both said rails so that the flat face of said bridge makes a certain constant dihedral angle within 0-10 arc minutes with the substrate plane and the gap between said flat face and said substrate plane has a width from 0 to 50 micron.

5. The monolayer or multilayer stack according to claim 1, wherein said collagen layer is made by the steps of:
    providing a first plate and a second plate, wherein said second plate is held substantially parallel to said first plate at a gap width of 0 to 50 microns, and wherein a collagen solution is captured between said first and second plates; and
    moving said second plate parallel to said first plate to generate suitable shearing force on said collagen solution to produce said collagen layer,
    wherein said first plate being held stationary during said moving step.

6. The monolayer or multilayer stack according to claim 1, further comprising at least one functional layer.

7. The monolayer or multilayer stack according to claim 6, wherein said functional layer is selected from any one or more of: lipid membrane, coagulant, living tissue cell layer, adhesion promotion layer, carrier layer, protective layer, delaminating promotion layer, and combinations thereof.

8. The multilayer stack according to claim 1, wherein said pit-like formations are disclination-like or vortex-like pores oriented normally to the plane of said collagen layer to provide channels for an interaction between said collagen layers within said stack.

9. The monolayer or multilayer stack according to claim 1, wherein said pit-like formations are filled with any one or more of: hydrogels, peptide based biomaterials, living tissue cell, and other bioactive materials like the incorporated ligands, encapsulated DNA, and growth factors or the combinations thereof.

10. The monolayer or multilayer stack according to claim 1, wherein the shear direction of each layer may not necessarily be parallel to each another.

11. The monolayer or multilayer stack according to claim 1, further comprising metal nanowires or carbon nanotubes.

12. The monolayer or multilayer stack according to claim 11, further comprises a plurality of cross-link fibers that connect one fiber bundle with an adjacent fiber bundle.

13. The monolayer or multilayer stack according to claim 11, wherein the director orientation of said fiber bundles varies in a random fashion from 0 to 360 degrees throughout the layer.

14. The monolayer or multilayer stack according to claim 1, wherein said collagen layer further comprises a plurality of vortex-like domains.

15. The monolayer or multilayer stack according to claim 14, wherein said collagen layer comprises a plurality of pores which lie in the approximate center of the vortex-like domain, wherein the center-to-center distance between adjacent pores range from 500 nanometers to 20 microns.

16. The monolayer or multilayer stack according to claim 1, wherein the maximum length of the pit lies in the range of 100 nanometers to 20 microns.

17. The monolayer or multilayer stack according to claim 12, wherein the center-to-center distance between said cross-link fibers lies in the range of 50 nanometers to 5 microns.

18. The monolayer or multilayer stack according to claim 1, wherein the depth of said pit is at least 50 nanometers.

19. A method of making monolayer or a multilayer stack having a collagen layer, wherein a surface of said collagen layer comprises a plurality of domains with predominant orientation of rod-like fibers in each of the domains, and a plurality of pit-like formations at the boundaries of said domains such that the domain orientation changes substantially continuously from one domain to another, said method comprising applying a shearing force to a collagen solution at a shear rate of $100\ s^{-1}$ or higher.

20. The method of claim 19 wherein the step of applying a shear force comprises conveying a collagen solution in the liquid phase through a slot-die type system at a shear rate of $1000^{s-1}$ or higher.

21. The method of claim 19 wherein the step of applying a shear force further comprises;
  providing a first plate and a second plate, wherein said second plate is held substantially parallel to said first plate at a gap width of 0 to 50 microns, and wherein a collagen solution is captured between said first and second plates; and
  moving said second plate parallel to said first plate to generate suitable shearing force on said collagen solution to produce said collagen layer.

22. A three-dimensional matrix for use in three-dimensional cell culture, said matrix comprises a collagen layer, said collagen layer comprises:
  a plurality of domains with predominant orientation of rod-like fibers in each of the domains, and
  a plurality of pit-like formations at the boundaries of said domains such that the domain orientation changes substantially continuously from one domain to another.

23. The three dimensional matrix of claim 22 wherein the collagen layer is prepared by shearing and drying on an anisotropic substrate with controlled pre-tilt angle more than two degrees.

24. The three-dimensional matrix according to claim 22, wherein said substrate is coated by anisotropic liquid crystal material.

25. The three-dimensional matrix according to claim 22, wherein said substrate is coated by polyamide like material with additional patterning and rubbing.

* * * * *